United States Patent [19]

Bartovský et al.

[11] 4,002,429
[45] Jan. 11, 1977

[54] METHOD AND APPARATUS FOR MEASURING THE CONCENTRATION OF COMBUSTIBLE COMPONENTS OF A GAS MIXTURE

[75] Inventors: Tomáš Bartovský; Jiří Sládeček, both of Prague, Czechoslovakia

[73] Assignee: Vysoka Skola Chemicko-technologicka, Prague, Czechoslovakia

[22] Filed: May 13, 1974

[21] Appl. No.: 469,453

[52] U.S. Cl. .............................. 23/254 E; 323/75 N
[51] Int. Cl.² .................................... G01N 27/16
[58] Field of Search ......... 23/232 E, 254 E, 255 E; 73/27; 323/16, 22 T, 75 E, 75 N

[56] References Cited

UNITED STATES PATENTS

| 3,347,635 | 10/1967 | McKee | 23/254 E |
|---|---|---|---|
| 3,379,960 | 4/1968 | May | 323/45 |
| 3,460,909 | 8/1969 | Gayle | 23/254 E |
| 3,461,724 | 8/1969 | Tong et al. | 323/75 N X |
| 3,522,010 | 7/1970 | Archer | 23/254 E |
| 3,574,555 | 4/1971 | Fertig | 23/254 E |
| 3,715,922 | 2/1973 | Menge | 323/75 E X |

*Primary Examiner*—Robert M. Reese

[57] ABSTRACT

A technique for measuring the concentration of combustible components of a gas mixture such as air by means of a catalytic bridge. The mixture to be analyzed is introduced into a closed chamber in which the catalytic portions of the bridge are located. After the bridge is electrically excited to heat the catalytic portions, the changes in the output bridge voltage resulting from burning of the gas by at the catalytic bridge element are measured over a prescribed interval to yield an indication proportional to the combustible component concentration. The prescribed interval is arranged to start after at least enough time has elapsed following the commencement of the electrical excitation of the bridge for the bridge to come to equilibrium under zero concentration conditions.

2 Claims, 4 Drawing Figures

# 4,002,429

METHOD AND APPARATUS FOR MEASURING THE CONCENTRATION OF COMBUSTIBLE COMPONENTS OF A GAS MIXTURE

BACKGROUND OF THE INVENTION

One known technique for measuring the concentration of combustible components of a gas mixture involves the catalytic burning of the gas in the vicinity of an oxygen-containing suitably reactive portion of an electric bridge. In this technique the gas to be analyzed continually passes (by flow or by diffusion) over the heated catalytic portion of the bridge so that when the latter is electrically excited the balance of the bridge is disturbed. The resultant changes in the absolute value of the bridge output are then measured continually or intermittently as a measure of the concentration of the gas components.

The disadvantage of known arrangements of this type is that the bridge output voltage variation during the described conditions of gas mobility are in practice influenced not only by the heat produced by the catalytic burning but also by changes, during the measuring cycle, in the ambient temperature and in the heat conductivity of the continually moving gas mixture. This is particularly true where the concentration of the combustible components in the mixture is low and/or where the mixture has a combustible gas concentration that is dynamically variable, e.g., where water vapor or carbon dioxide are present.

While theoretically such disturbing influences can be offset to some degree by designing the bridge so that the catalytic and reference branches receive exactly the same gas flow and exhibit exactly the same geometric and electric characteristics, such conditions are extremely difficult to obtain in practice.

SUMMARY OF THE INVENTION

The method and apparatus of the present invention avoid these disadvantages by effectively and reliably measuring small concentrations of combustible components of an oxygen-containing gas mixture over a wide range of ambient conditions, using the catalytic burning technique. The catalytic portions of the catalytic bridge is situated in a closed chamber which is initially filled with the gas mixture to be analyzed, and the gas is burned by electrically exciting the bridge to heat the catalytic portion. The changes in the electrical characteristics of the bridge that accompany the changes in temperature of the catalytic portions while the combustible components of the gas are being burned are measured after the elapse of a prescribed interval following the commencement of the electrical excitation of the bridge. Such prescribed interval is made at least equal to the time necessary for the bridge to reach equilibrium when the gas mixture in the chamber has a zero concentration of combustible components.

Facilities may be provided for converting the electrical variations of the bridge into continuous variations of output voltage or alternatively into a plurality of discrete step-like variations of the output voltage. In the latter case, the detection of the number of steps of minimum predetermined amplitude occurring over the measuring interval is indicative of the combustible component concentration of the mixture.

BRIEF DESCRIPTION OF THE DRAWING

The invention is further set forth in the following detailed description taken in conjunction with the appended drawing, in which.

DETAILED DESCRIPTION

Figure 1:
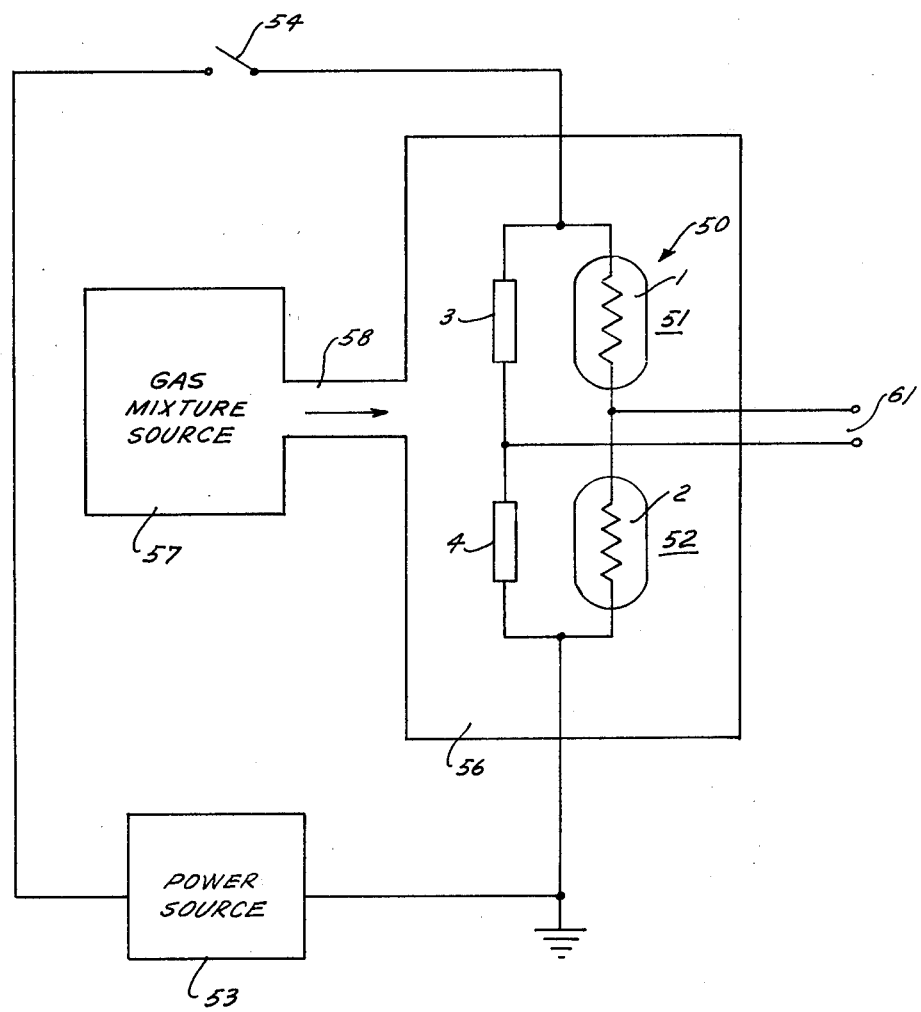
FIG. 1 is a pictorial representation of a catalytic bridge employed in the technique of the present invention, illustrating an arrangement for introducing the gas mixture into and burning the mixture by contact with heated catalytic facilities of the bridge.

Referring now to the drawing, FIG. 1 illustrates schematically a catalytic electric bridge 50 of the type useful for the purposes of the present invention. The bridge includes a measuring arm 51 which has a filament 1 coated with a catalytic material. (Alternatively, the measuring arm may include a filament embedded inside a ceramic body having a catalytic surface of the type just indicated.) Such designs of the catalytic bridge facilities are well-known in the art.

A reference arm 52 of the bridge, also in the form of a filament 2, is assumed to have the characteristics of the measuring arm 51 except that the arm 52 is not provided with a catalytic coating on the filament. The bridge also includes a pair of balance arms 3 and 4 embodied by resistors.

Electrical excitation of the bridge is accomplished by coupling a power source 53 to the junctions of the arms 51 and 3 and the arms 52 and 4, respectively, via a switch 54. As a result of such excitation, the catalytic filament 1 is heated.

The bridge 50 is suitably mounted in a chamber 56 into which a gas mixture from a source 57 is introduced via an inlet pipe 58. When the gas mixture comes in contact with the catalytic filament 1 of the bridge, its combustible components are suitably burned. The temperature change accompanying the resultant reaction changes the resistance of the associated arm 51 and alters the electrical conditions of the bridge when the latter is electrically excited. Such alterations in turn lead to variations of the bridge output voltage appearing, on lines 61 extending respectively from the junctions of the arms 51, 52 and 3, 4. The absolute magnitude of the voltage output of the bridge is proportional to the concentration of the burned combustible components in the gas mixture to be analyzed.

Figure 2:
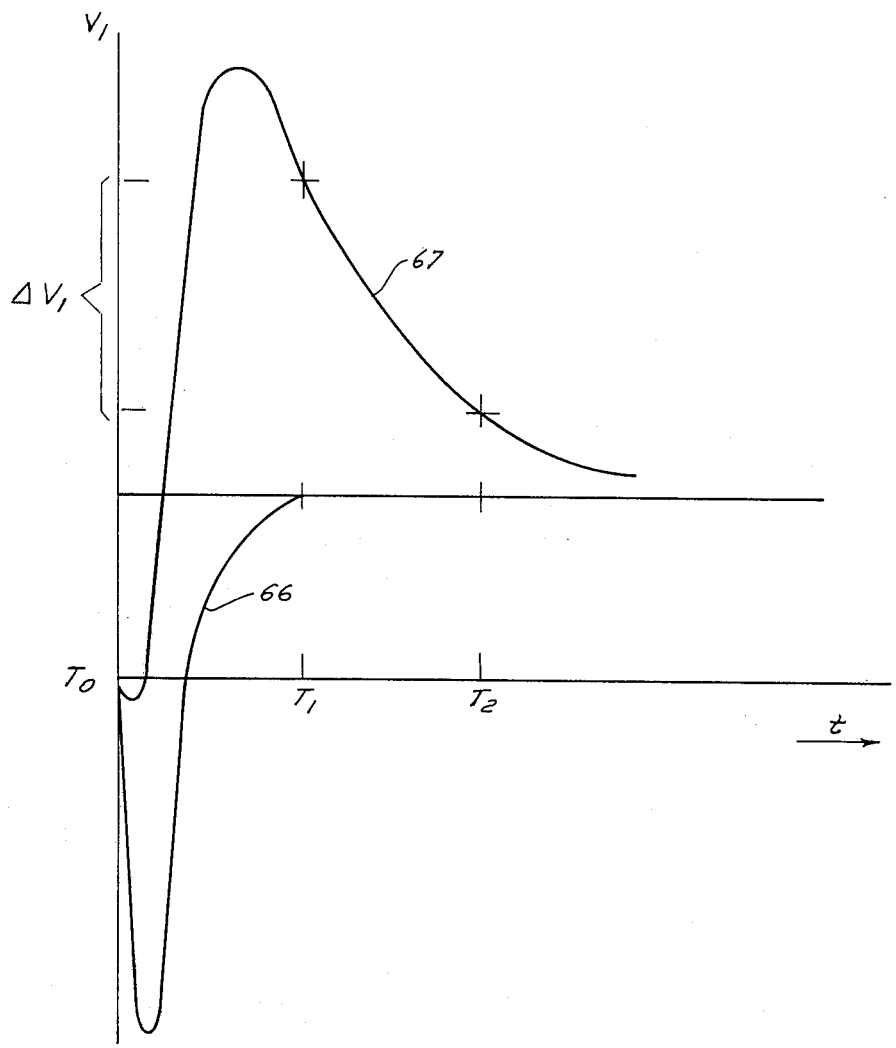
FIG. 2 is a set of curves showing the output voltage characteristic of a catalytic bridge as a function of time after the bridge is electrically excited, for the respective cases of zero concentration and a typical finite concentration of the combustible components of the gas to be analyzed.

The curves of FIG. 2 show typical time courses of the output voltage $V_1$ on the lines 61. The time T0 shown on the figure is assumed to be the time at which electrical excitation commences for the bridge 50 by closure of the switch 54. A curve 66 represents the voltage course for a gas mixture having a zero concentration of combustibles, while a curve 67 shows the voltage course for a typical finite degree of concentration of the combustibles. The curve for zero concentration reaches a steady state condition at a time T1. It has been found preferable, for purposes of the invention, that the processing of the output voltage of the bridge to derive a quantity indicative of the actual concentration of impurities in the gas be retarded by a predetermined time at least equal to T1.

Figure 3:
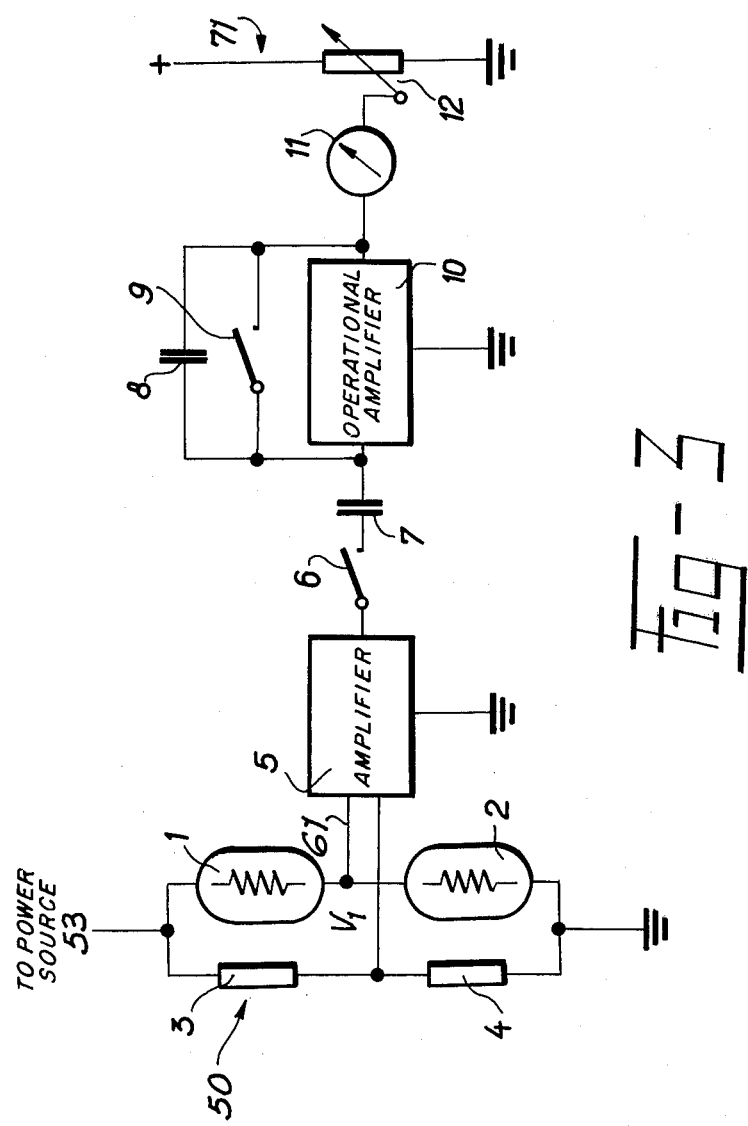
FIG. 3 is a combined block and schematic diagram of one arrangement for processing the voltage output of the bridge of FIG. 1 to obtain a continuous indication representative of the concentration of the combustible components in the gas.
Figure 4:
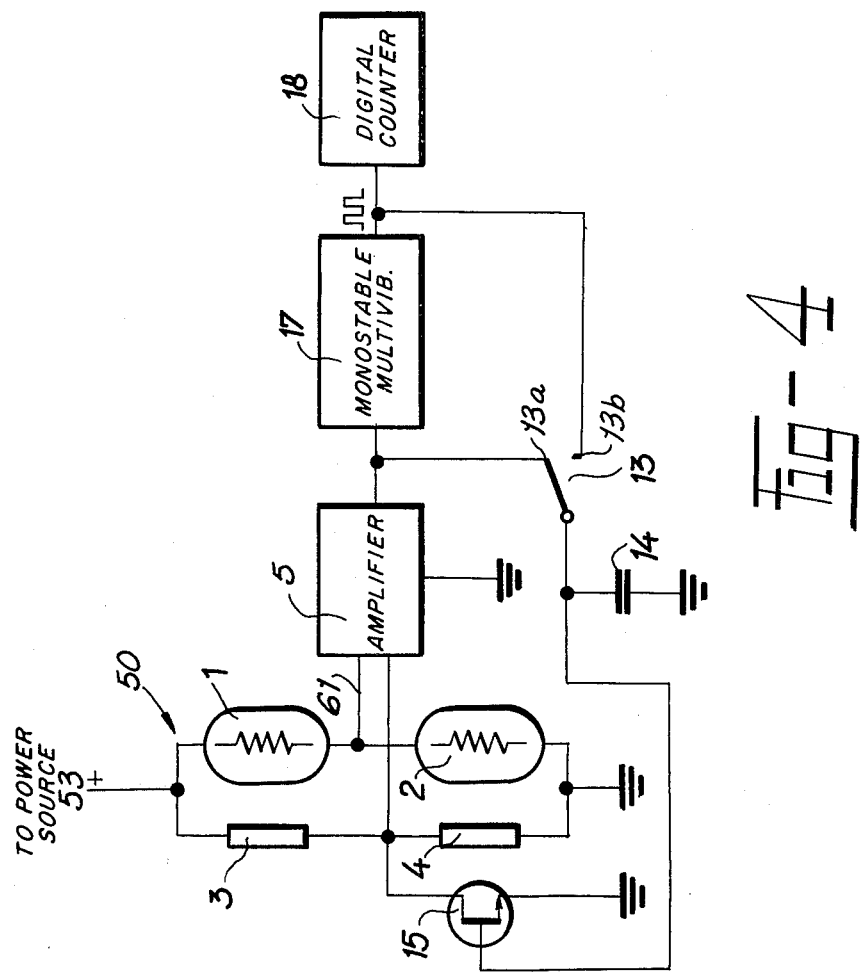
FIG. 4 is a combined block and schematic diagram of an alternative arrangement for processing the output of the bridge of FIG. 1 to obtain a discrete indication representative of the concentration of the combustible components in the gas.

In further accordance with the invention, arrangements for processing the bridge output voltage are shown in alternative embodiments in FIGS. 3 and 4. The chamber, gas mixture source and burner have been omitted in FIGS. 3 and 4 for clarity. Referring to FIG. 3, for example, the output on lines 61 is a continuous voltage applied through an amplifier 5 and a first normally open, timer-operated switch 6 to a first capacitor 7. The output of the capacitor 7 is applied to the input of an operational amplifier 10. The output of the amplifier 10 is fed back through a second capacitor 8 to its input. A normally open, timer-operated second switch 9 shunts the second capacitor 8. The output of the amplifier 10 is applied to a voltmeter 11 whose zero setting may be calibrated via a wiper arm 12 of a potentiometer 71.

The output voltage of the operational amplifier 10 in this arrangement may be represented as $$K \int_{T1}^{T2} \left(\frac{dV1}{dt}\right) dt + C_1 \qquad \text{[EQUATION 1]}$$

where V1 is the output voltage of the bridge, K is a proportionally constant depending on the amplification of amplifier 5 and on the capacitance ratio of the capacitors 7 and 8, and C is an integration constant controlled by the initial conditions established for the arrangement of FIG. 3. From Equation 1, the output voltage of the operational amplifier is proportional to $$|\Delta V1|_{T1}^{T2}, \qquad \text{[EQUATION 2]}$$

i.e., the output voltage of the operational amplifier is directly proportional to the variation of the output voltage of the bridge within the time interval T1 — T2. The time $T_2$ is selected so that, as shown in FIG. 2, the interval $T_2 - T_1$ falls within the relatively high-slope portion of the trailing edge of the curve 67 and corresponds to a relatively large value of $\Delta V_1$.

The operational of the arrangement of FIG. 3 is as follows:

Following the filling of the chamber 56 with the gas to be analyzed, the bridge is energized at the time T0 so that the catalytic filament 1 may change its impedance in accordance with temperature changes resulting from the burning of the combustible components in the gas. The change in bridge balance under these conditions is manifested as a change in output voltage on the lines 61. During the interval between T0 and T1, the zero-setting of the voltmeter 11 may be established with the aid of the potentiometer 71, while the initial conditions of the operational amplifier 10 may be set by closing the switch 9.

At the instant T1 the switch 9 is opened and the switch 6 is closed, so that the voltage at the output of the amplifier 5 is applied via the capacitor 7 to the operational amplifier 10. Upon the conclusion (at a predetermined time T2) of the measurement interval, the switch 6 is re-opened. During the interval T1 to T2, the change in the voltage established on the voltmeter 11 is proportional to the concentration of combustible gas components in the mixture within the chamber 56. If desired, the scale of the voltmeter 11 can be calibrated directly in terms of units of concentration.

In the alternative embodiment shown in FIG. 4, the output of the amplifier 5 is applied to a capacitor 14 through a first position 13a of a timer-operated switch 13. The output of the capacitor 14 is applied to a gate of a field-effect transistor 15. The source-drain path of the transistor 15 is coupled to the junction of the resistors 3 and 4 in the bridge 50 so that the electrical balance of the bridge may be varied in proportion to the instantaneous current flowing in the source-drain path. Such current, in turn, is proportional to the voltage applied from the capacitor 14 to the high-impedance gate electrode of the transistor 15.

The output of the amplifier 5 is also applied to the input of a threshold-triggered monostable multivibrator 17. The latter responds to a voltage step of predetermined minimum amplitude at the input thereof to generate an output pulse which is coupled via a second position 13b of the switch 13 across the capacitor 14. The output of the multivibrator 17 is also coupled to the input of a digital counter 18.

In the operation of the arrangement of FIG. 4, the preliminary steps of introducing the gas into the chamber 56, and the burning of the gas at the filament 1 via the electrical excitation of the bridge at time T0 are identical to that in the operation of FIG. 3. During such preliminary operations (which are also assumed to take place up to the time T1), the counter 18 is suitably initialized and the switch 13 is set at its upper position 13a.

At the commencement of the measurement interval T1, the switch 13 is moved to its lower position 13b to establish the feedback path from the output of the multivibrator 17 to the gate of the transistor 15 via the capacitor 14. During the measurement interval, the course of the voltage on the lines 61 proceeds in a step-wise discrete manner because of the action of the multivibrator 17. In particular, at the start of the measurement interval, the voltage from the bridge, as augmented by the amplifier 5, is of sufficient amplitude to trigger the multivibrator 17 so that the output pulse thereof will increment the capacitor 14 by a small voltage magnitude $\Delta V$. Such voltage increment is applied to the gate of transistor 15 so that the resulting proportional change in current at the output of the transistor serves to further unbalance the bridge. The resultant second step is again applied via amplifier 5 to the input of the multivibrator 17, which causes a second increment of voltage to be applied to the capacitor 14, and so forth. Because of this action, the voltage difference between times T1 and T2 shown in the curve 67 will be traced out in a step-wise manner, with the number of steps being proportional to the magnitude of the voltage difference. Consequently, the number of counts accumulated in the counter 18 from the pulses at the output of the multivibrator 17 will be directly proportional to the voltage difference at the output of the bridge over the measurement interval and thereby to the percentage concentration of the combustible components of the gas mixture under test.

With either of the arrangements described above, disturbing influences such as changes of the heat conductivity of the analyzed gas mixture, changes of the ambient temperature, etc., are substantially suppressed; and since in the measurement interval T1 to T2 there is no significant movement of gas over the sensing elements of the bridge, any dependence of the readings of the voltmeter 11 or the counter 18 based on such movement of gas is eliminated. Consequently, measuring errors can be easily maintained within the range of $\pm 10^{-4}$% in volume, even where the combustible constituents of the gas are strongly variable.

In the foregoing, the invention has been described in connection with preferred techniques thereof. Many variations and modifications will now occur to those skilled in the art. It is accordingly desired that the scope of the appended claims not be limited to the specific disclosure herein contained.

What is claimed is:

1. For use with a catalytic electrical bridge wherein the burning of combustible components of a gas mixture in the catalytic portion of the bridge is effective to cause changes in the electrical balance of the bridge when the latter is electrically excited, an improved arrangement for efficiently measuring small concentrations of the combustible gas components in the gas mixture, which comprises:

means positioning the catalytic facilities of the bridge in a closed chamber;

means introducing the gas mixture into the closed chamber to be catalytically burned, thereby to induce changes of the output voltage of the bridge, when the latter is electrically excited in accordance with a characteristic that reaches equilibrium over a first interval following the commencement of excitation of the bridge when the concentration of combustible gas components in the mixture is zero;

means operative for exciting the bridge;

first and second capacitors;

switching means rendered effective at the conclusion of the first predetermined interval following the operation of the bridge exciting means and operable over a pescribed second interval for coupling the bridge output voltage to the input of the first capacitor;

an operational amplifier;

means for coupling the output of the first capacitor to the input of the operational amplifier; and means for coupling the second capacitor between the output of the operational amplifier and the input thereof, whereby the voltage output of the operational amplifier during the prescribed second interval is indicative of the change of the bridge output voltage over the prescribed second interval.

2. For use with a catalytic electrical bridge wherein the burning of combustible components of a gas mixture in the catalytic portion of the bridge is effective to cause changes in the electrical balance of the bridge when the latter is electrically excited, an improved arrangement for efficiently measuring small concentrations of the combustible gas components in the gas mixture, which comprises:

means positioning the catalytic facilities of the bridge in a closed chamber;

means introducing the gas mixture into the closed chamber to be catalytically burned, thereby to induce changes of the output voltage of the bridge, when the latter is electrically excited in accordance with a characteristic that reaches equilibrium over a first interval following the commencement of excitation of the bridge when the concentration of combustible gas components in the mixture is zero;

means operative for exciting the bridge;

a field-effect transistor whose source-drain path is connected to a junction of the bridge;

a capacitor connected to the gate of the field-effect transistor;

a threshold-operated monostable multivibrator having an input coupled to the output of the bridge for generating a pulse each time a voltage step at its input exceeds a predetermined value; and switching means rendered effective at the conclusion of the first predetermined interval following the operation of the bridge exciting means and operable over a second prescribed interval for coupling the output of the multivibrator to the capacitor to increment the voltage across the capacitor and thereby the voltage at the base of the field-effect transistor, whereby the number of pulse occurrences at the output of the multivibrator during the second prescribed interval is made indicative of the change of the bridge output voltage over the prescribed second interval.

* * * * *